United States Patent
Bouchard Fortin et al.

(10) Patent No.: US 11,510,814 B2
(45) Date of Patent: Nov. 29, 2022

(54) ELECTRIC GOGGLES FOR PREVENTING FOGGING IN COLD WEATHER CONDITIONS

(71) Applicant: KIMPEX INC., Drummondville (CA)

(72) Inventors: Nicolas Bouchard Fortin, Racine (CA); Étienne Gilbert, Beloeil (CA); Stéphane Dion, Sainte-Cécile de Milton (CA)

(73) Assignee: KIMPEX INC., Drummondville (CA)

(*) Notice: Subject to any disclaimer, the term of this patent is extended or adjusted under 35 U.S.C. 154(b) by 884 days.

(21) Appl. No.: 15/637,065

(22) Filed: Jun. 29, 2017

(65) Prior Publication Data
US 2019/0000674 A1 Jan. 3, 2019

(51) Int. Cl.
*A61F 9/02* (2006.01)
*A42B 3/04* (2006.01)
*G02C 11/08* (2006.01)
*G02C 11/00* (2006.01)
*A42B 3/18* (2006.01)
*A42B 3/24* (2006.01)

(52) U.S. Cl.
CPC .............. *A61F 9/02* (2013.01); *A42B 3/042* (2013.01); *A42B 3/185* (2013.01); *A42B 3/245* (2013.01); *A61F 9/028* (2013.01); *G02C 11/08* (2013.01); *G02C 11/10* (2013.01); *A61F 9/027* (2013.01)

(58) Field of Classification Search
CPC ............. A61F 9/028; A61F 9/02; A42B 3/042
See application file for complete search history.

(56) References Cited

U.S. PATENT DOCUMENTS

| 1,963,990 | A | * | 6/1934 | Gilkeson | G02C 11/08 2/435 |
|---|---|---|---|---|---|
| 4,150,443 | A | * | 4/1979 | McNeilly | A61F 9/028 2/171.3 |
| 4,638,728 | A | * | 1/1987 | Elenewski | B62J 33/00 2/435 |
| 4,686,712 | A | * | 8/1987 | Spiva | A42B 3/185 2/10 |
| 4,918,753 | A | * | 4/1990 | Mermillod | A42B 3/185 2/10 |
| 4,942,629 | A | * | 7/1990 | Stadlmann | A61F 9/02 2/435 |
| 5,954,650 | A | * | 9/1999 | Saito | G06T 11/00 382/128 |
| 6,701,537 | B1 | * | 3/2004 | Stamp | H05B 3/84 2/424 |

(Continued)

*Primary Examiner* — Alissa J Tompkins
*Assistant Examiner* — Brieanna Szafran
(74) *Attorney, Agent, or Firm* — Myers Bigel, P.A.

(57) ABSTRACT

A pair of electric goggles is disclosed. The goggles include a conductive lens mounted onto a frame adapted to be electrically connected to an electric socket in order to raise the temperature of the lens, when powered. The goggles are provided with a strap for attaching to a helmet, the strap has a strap clip designed to have the electric socket attached thereto. The electric socket is meant to be electrically connected to a power supply via a power cable. With the combination of a strain relief clip located below the electric socket, the power cable can be positioned in a predetermined configuration, which unencumbers the user from the power cable when detaching or removing the goggles.

22 Claims, 10 Drawing Sheets

(56) References Cited

U.S. PATENT DOCUMENTS

| | | | | |
|---|---|---|---|---|
| 6,845,548 B1* | 1/2005 | Lin | ............... | A42B 3/185 |
| | | | | 2/10 |
| 7,033,209 B2 | 4/2006 | Swiatek et al. | | |
| 7,438,410 B1* | 10/2008 | Howell | ............... | G02C 11/00 |
| | | | | 351/158 |
| 8,555,423 B2* | 10/2013 | Giroux | ............... | A61F 9/027 |
| | | | | 2/422 |
| 9,015,868 B2* | 4/2015 | Matsumoto | ............ | A42B 3/245 |
| | | | | 2/435 |
| 9,072,331 B2 | 7/2015 | McNeal | | |
| 9,301,879 B2* | 4/2016 | McCulloch | ............ | A61F 9/027 |
| 2003/0126723 A1* | 7/2003 | McNeal | ............... | A44B 11/12 |
| | | | | 24/163 R |
| 2011/0072564 A1* | 3/2011 | Krauter | ............... | A42B 3/185 |
| | | | | 2/422 |
| 2012/0180202 A1* | 7/2012 | McNeal | ............... | A42B 3/185 |
| | | | | 2/422 |
| 2013/0091623 A1* | 4/2013 | McCulloch | ............ | A61F 9/029 |
| | | | | 2/435 |
| 2014/0317836 A1* | 10/2014 | McCulloch | ............ | G02C 11/08 |
| | | | | 2/435 |
| 2014/0374402 A1* | 12/2014 | Cornelius | ............... | A61F 9/028 |
| | | | | 219/211 |
| 2016/0044747 A1* | 2/2016 | Prins | ............... | A61F 9/029 |
| | | | | 219/211 |
| 2017/0128267 A1 | 5/2017 | Rees et al. | | |
| 2017/0143549 A1* | 5/2017 | Becker | ............... | G06F 3/005 |

\* cited by examiner

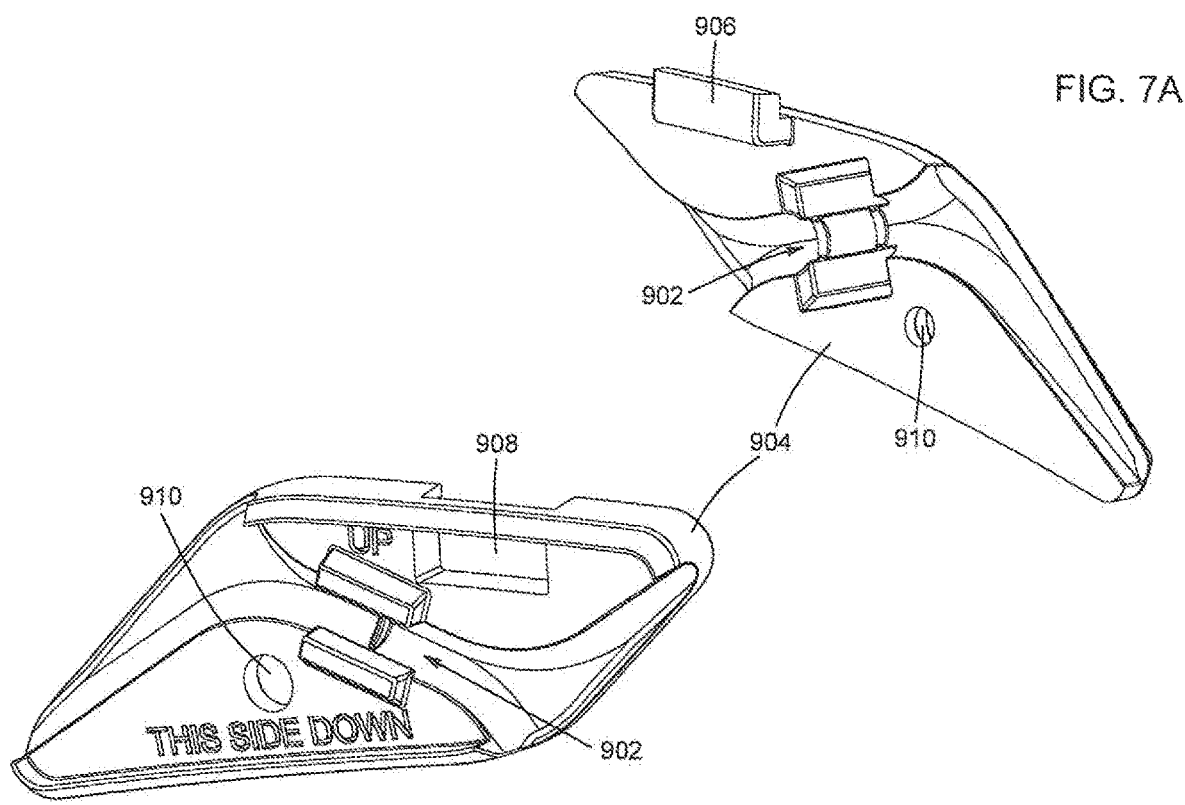

ELECTRIC GOGGLES FOR PREVENTING FOGGING IN COLD WEATHER CONDITIONS

TECHNICAL FIELD

The technical field generally relates to electric goggles and more specifically relates to electric goggles for preventing fogging in cold weather conditions and suitable for use in combination with a helmet.

BACKGROUND

Frost or condensation formation on the lenses of goggles used for practicing winter sports and outdoor activities is undesirable. Some cold-weather goggles presently on the market are provided with a heated lens to prevent or reduce frost or condensation on the lens.

Electric goggles typically include conductive strips and/or a resistive coating. Current is circulated through the coating or strips, which generates heat, effectively eliminating fog or frost accumulation on the lens. Electric goggles of various designs have been proposed for use in outdoor activities such as snowmobiling and skiing. One drawback of existing electric goggles is the discomfort that often results from the electric wires and components needed to bring the current to the lens. Electrical connections on the frame unbalances the weight of the goggles. In the case of snowmobiling, riders often forget about the electric wire connected to the power source when they get off their snowmobile, creating stress on the components by involuntarily pulling them. In addition, users often need to place and replace their goggles from the top or side of their helmet to their face, and the electric components are often in the way when manipulating the goggles.

In view of the above, many challenges still exist in the field of electric goggles.

SUMMARY

According to an aspect, electric goggles for preventing fogging in cold weather conditions are provided. The electric goggles include a frame, a conductive lens housed within the frame and a resilient strap having a frame end and a clip end. The frame end of the strap is attached to the frame and the clip end is spaced away from the frame end by a portion of the resilient strap. The goggle also includes a strap clip attached to the clip end of the resilient strap. The strap clip comprises an electric socket for receiving therein the plug of a power cable, for powering the conductive lens. The goggle also comprises at least one electrical wire running along that portion of the resilient strap that extend between the frame and clip ends, electrically connecting the conductive lens and the electric socket.

According to another aspect, the electric goggles includes a frame, a conductive lens in the frame and a resilient strap attached to the frame. An electric socket in mounted on the resilient strap, and is located remotely from the frame. The electrical wires run along a portion of the resilient strap to connect the conductive lens to the socket.

Yet according to another aspect, the electric goggles includes a frame, a conductive lens housed within the frame, the lens including resistive elements. The goggle includes the resilient strap attached to the frame, and a strap clip attached the strap and disposed proximate the ears of the wearer when he wears the goggles on his helmet. The strap clip includes an electrical socket connectable to a power cable, for powering the resistive elements of the conductive lens. The goggle also includes an electrical wire extending from the electrical socket to another electrical wire of the conductive lens.

Yet according to another aspect, a helmet in combination with any embodiment of the electric goggles described above is provided. The helmet includes an attachment system comprising a pair of studs, provided on the right and left sides of the helmet. In this particular embodiment, the electric goggles includes two resilient straps, provided on the right and left sides of the frame of the goggles. The first resilient strap is provided with the strap clip with the electric socket described above, and includes slot for attaching to one of the studs of the helmet. The other resilient strip is provided with an attachment clip having a slot, for attaching to other one of the studs of the helmet. In use, the strap clip with the electric socket is located near one of the helmet studs, and thus near one of the pivot points of the goggles, preventing the wearer to inadvertently touch the electric socket and/or power cable when grabbing the frame of the goggle to place them on top the of the helmet.

BRIEF DESCRIPTION OF THE DRAWINGS

FIG. 7A is a perspective view of a component of the strain relief clip in accordance with an embodiment.

FIG. 7B is a perspective view of a complementary component to the component shown in FIG. 7A.

DETAILED DESCRIPTION

It should be understood that the elements of the drawings are not necessarily depicted to scale, since emphasis is placed upon clearly illustrating the elements and structures of the present embodiments. In the following description, the same numerical references refer to similar elements. Furthermore, for the sake of simplicity and clarity, namely so as to not unduly burden the figures with several reference numbers, not all figures contain references to all the components and features, and references to some components and features may be found in only one figure, and components and features of the present disclosure which are illustrated in other figures can be easily inferred therefrom. The embodiments, geometrical configurations, materials mentioned and/or dimensions shown in the figures are optional, and are given for exemplification purposes only.

Figure 1:
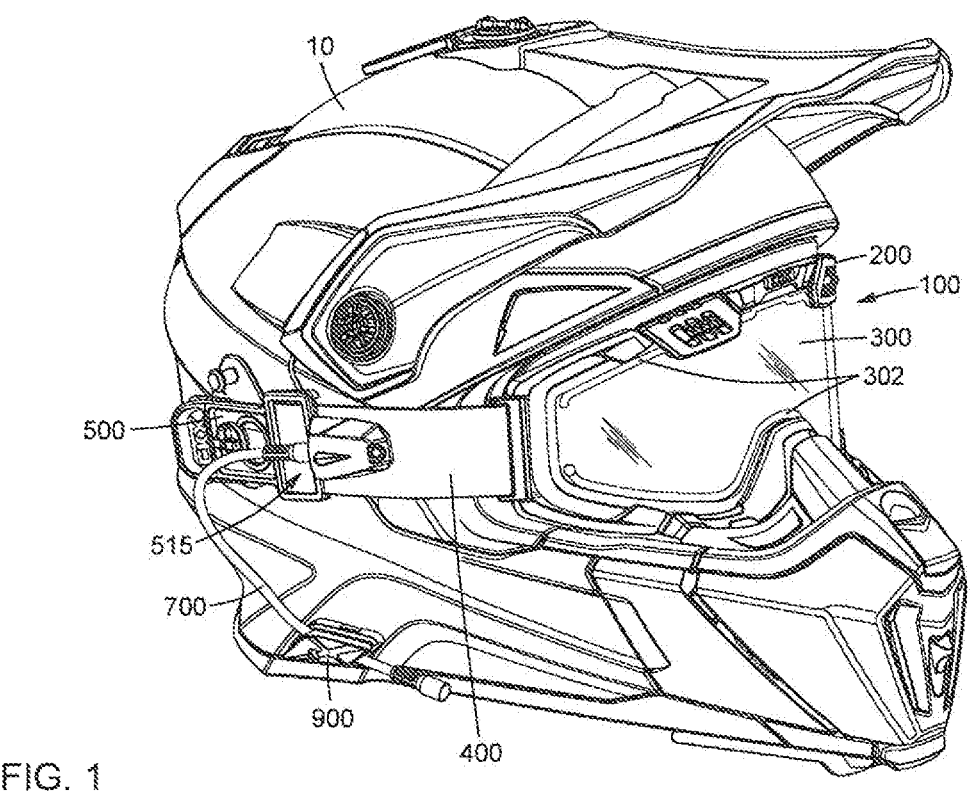
FIG. 1 is a side perspective view of a pair of electric goggles attached to a helmet in a fitted configuration, in accordance with an embodiment.

FIGS. 1 through 9 illustrate a pair of electric goggles 100 in accordance with various possible embodiments. Referring more specifically to FIG. 1, the electric goggles 100 are illustratively presented in a fitted or "in use" configuration where the electric goggles 100 are worn in combination with a helmet 10. In this embodiment, the electric goggles 100 comprise a frame 200 onto which a conductive lens 300 is mounted. The goggles 100 can further comprise at least one resilient strap 400 extending from the frame 200, and a strap clip 500 provided at the end of the strap 400 to allow the goggles 100 to be attached to the helmet 10. In the present embodiment, the lens 300 is a conductive lens provided with a heating assembly and the strap clip 500 can comprise an electrical assembly 515 for providing an electrical current to said heating assembly of the conductive lens 300, therefore effectively heating up the lens 300. In this manner, the goggles 100 are thus particularly adapted and configured to prevent fog accumulation or condensation on the conductive lens 300, especially in cold weather conditions and/or during outdoor activities such as skiing or riding a snowmobile.

It should be understood that, as used herein, the expression "resilient strap" can refer to the strap's ability to cope with changes occurring to it and/or around it, such as a change in length resulting from the application of force or pressure, or a change in surrounding temperatures for example. Likewise, the expression "conductive lens" should be understood to refer to of the lens' ability to conduct an electric current across a surface of the lens via conductive elements in a manner that will be described herein below.

Figure 2A:
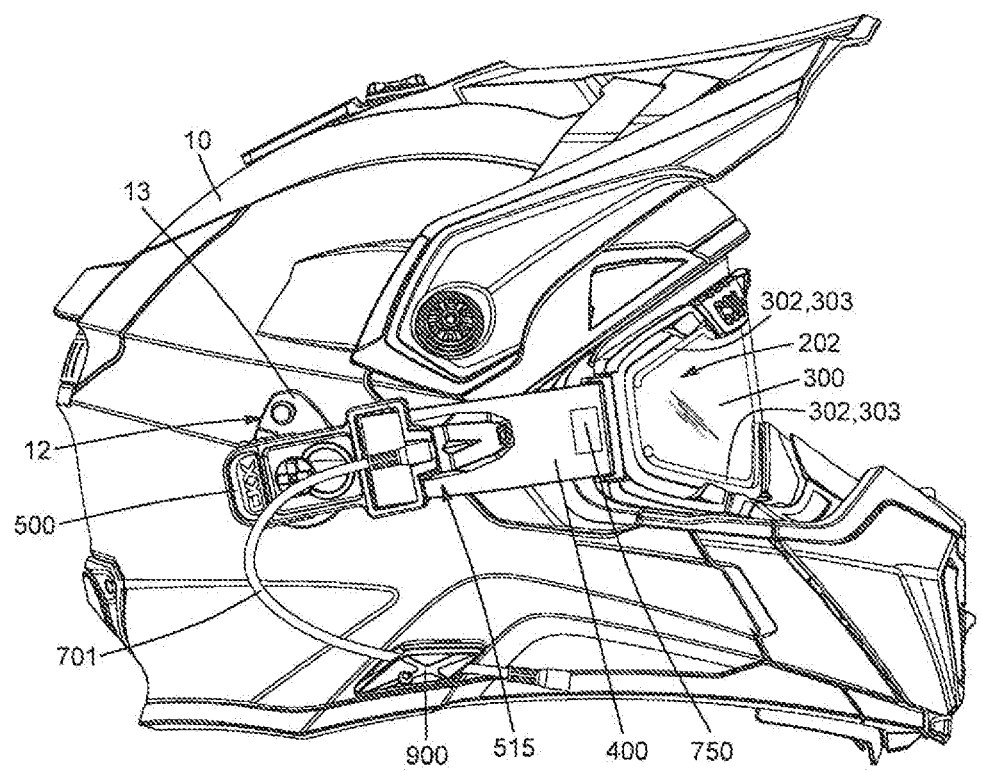
FIG. 2A is a side view of the electric goggles of FIG. 1.
Figure 2B:
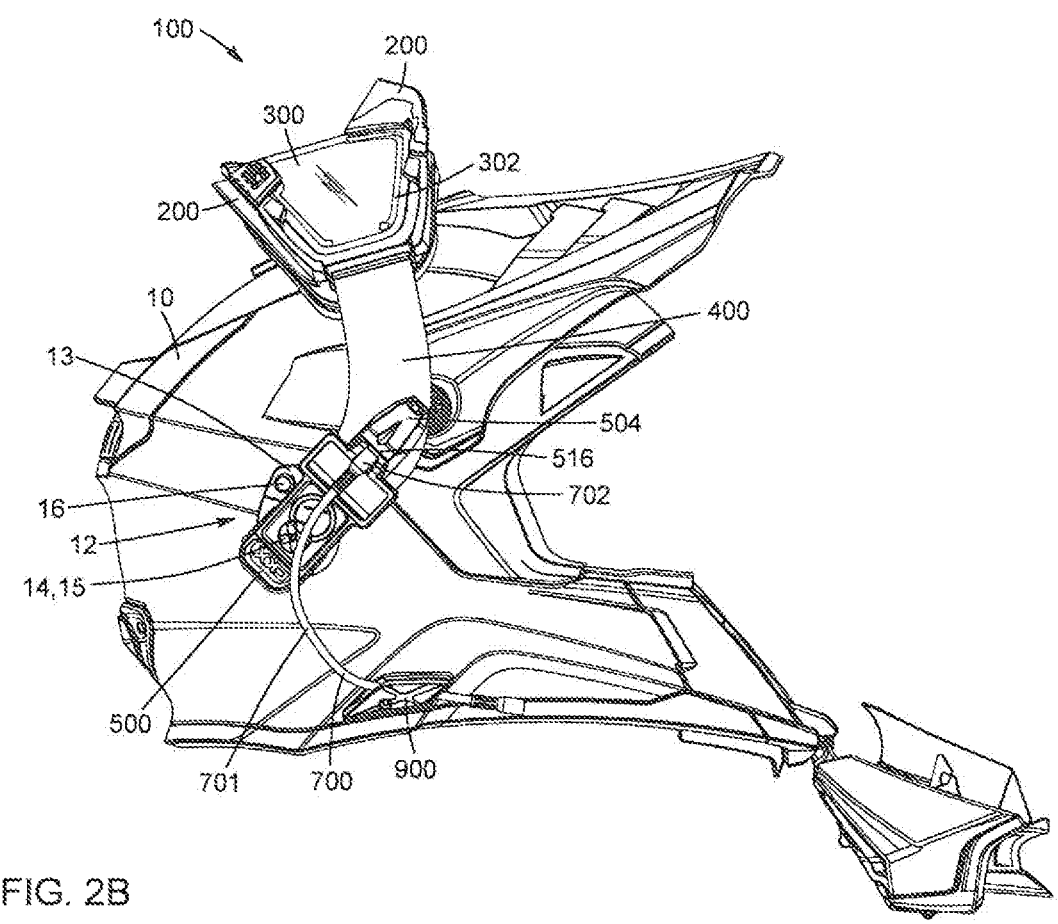
FIG. 2B is a side view of the electric goggles attached to a helmet in a rotated configuration, in accordance with an embodiment.
Figure 3:
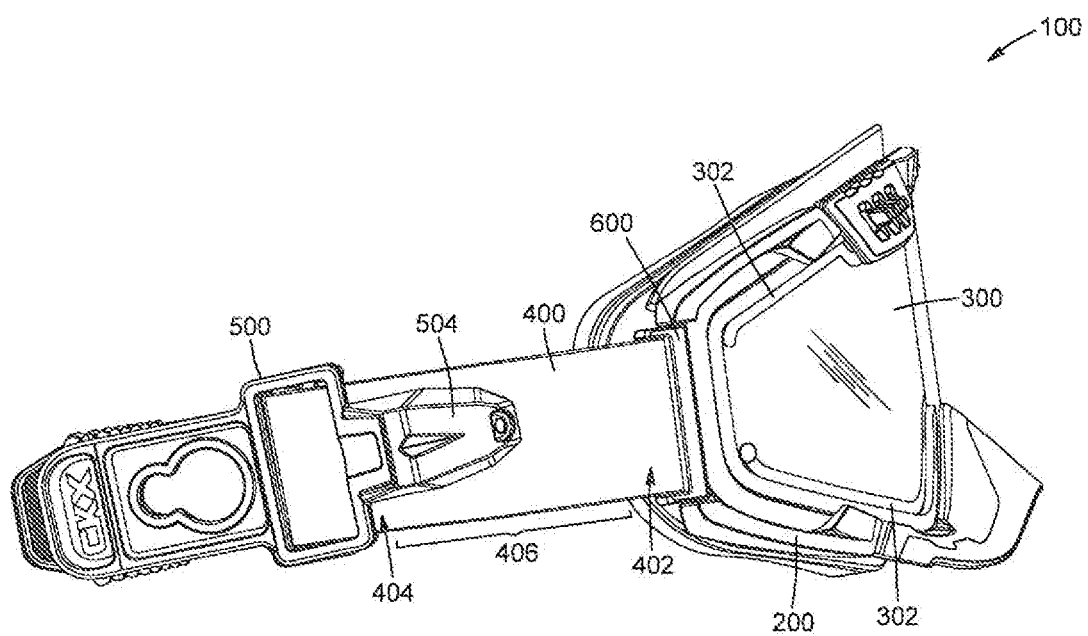
FIG. 3 is a side view of the electric goggles.

Now referring to FIGS. 2A to 3, in addition to FIG. 1, the frame 200 of the electric goggles 100 defines a frame opening 202 through which a user can see when wearing the electric goggles 100. In this embodiment, the conductive lens 300 can be shaped and sized to fit within the frame opening 202 in order to protect the user's eyes and face from wind and debris when riding a snowmobile, for example. Furthermore, the conductive lens 300 comprises a heating surface which can be provided with a heating assembly to heat up said heating surface and effectively raise the temperature of the conductive lens 300. In this embodiment, the heating assembly comprises a resistive coating, (typically a metallic coating), covering the heating surface of the conductive lens 300 and further comprises conductive elements 302 respectively provided on opposed top and bottom portions of the heating surface. The conductive elements 302 can act as respective positive and negative terminals between which an electrical current can travel. The conductive elements can be conductive strips provided on opposite sides of the conductive lens. As such, the metallic coating acts as a resistive element of the heating assembly which produces heat in order to raise the temperature of the conductive lens 300. It should be understood that the expression "resistive" can refer to electrical resistance, which in turn refers to the measure of difficulty encountered by a travelling electrical current. As such, the term "resistive element" refers to the electrical resistance of the metallic coating of the heating assembly. Alternatively, the conductive elements 302 can be positioned in any suitable configuration across the conductive lens 300, in order to have the electrical current travel therebetween so as to raise the temperature of said lens 300 to remove or prevent fog accumulation.

As mentioned above, the electric goggles 100 can be further provided with at least one resilient strap 400 adapted for attaching the frame 200 to a helmet 10 worn by the user. In this embodiment, the resilient strap 400 of the goggles 100 is provided with opposed first and second ends. The first end of the resilient strap 400 can be a frame end 402 adapted to be attached to the frame 200 of the goggles 100 via a frame fastener 600. The second end of the resilient strap 400 can be a clip end 404, the clip end 404 being provided with a strap clip 500 configured to attach the resilient strap 400 to the helmet 10 via an attachment system 12. In the present embodiment, both ends of the resilient strap 402, 404 can be separated by a portion of the resilient strap 406, effectively spacing the clip end 404 away from the frame end 402 of the strap 400. As such, the clip end 404 of the resilient strap 400, and thus the strap clip 500, are positioned proximate to the user's ear, effectively separating the electric socket 516 from the frame 200 by about 1 to 3 inches for example. In the illustrated embodiment of FIG. 8A, the resilient strap 400 is a first strap which extends from a first side of the frame 200 and the electric goggles 100 can comprise a second resilient strap 400' which extends from a second side of the frame 200. The first and second straps 400, 400' are adapted for attaching the frame 200 to respective left and right sides of the helmet 10. Alternatively, the goggles 100 can comprise a single resilient strap 400, as illustrated in FIG. 81, adapted to extend from one side of the frame 200 to the other and surround the helmet 10 in a manner such as is commonly known in the art.

Still referring to FIGS. 2A to 3, the attachment system 12 of the present embodiment allows the goggles 100 to be removably attached to the helmet 10 for quick and easy attachment/detachment of the goggles 100 from the helmet 10 providing accessibility and breathability to the user's face. In this embodiment, the attachment system 12 comprises an attachment support 13 provided on at least one side of the helmet 10 and a helmet stud 14 extending outwardly from the attachment support 13. Alternatively, the helmet stud 14 can be molded directly on the helmet 10 and extend therefrom to define the attachment system 12. The helmet stud 14 can define a pivot point 15 and can be adapted for pivotally attaching the strap clip 500 of the resilient strap 400 thereto. This feature of the present embodiment of the electric goggles 100 allows the user to rotate the goggles 100 about the helmet stud 14 in order to position the goggles 100 on top of the helmet 10 in a rotated configuration as illustrated in FIG. 2B. By "rotated" or "pivoted" configuration, it is meant that the goggles are not in use, and are positioned on top of the helmet. The rotated configuration of the electric goggles 100 can allow the user to effectively remove the goggles 100 from in front of his eyes when needed without having to detach or remove the goggles 100 from the helmet 10. In this embodiment, the attachment support 13 can be further provided with a protrusion 16 adapted for blocking the rotation movement of the goggles 100 about the helmet stud 14 at a predetermined angle. More specifically, the protrusion 16 can come into contact with the strap clip 500 when the goggles 100 are rotated about the helmet stud 14 on top of the helmet 10 in order to prevent the goggles 100 from falling behind the helmet 10.

Figure 4A:
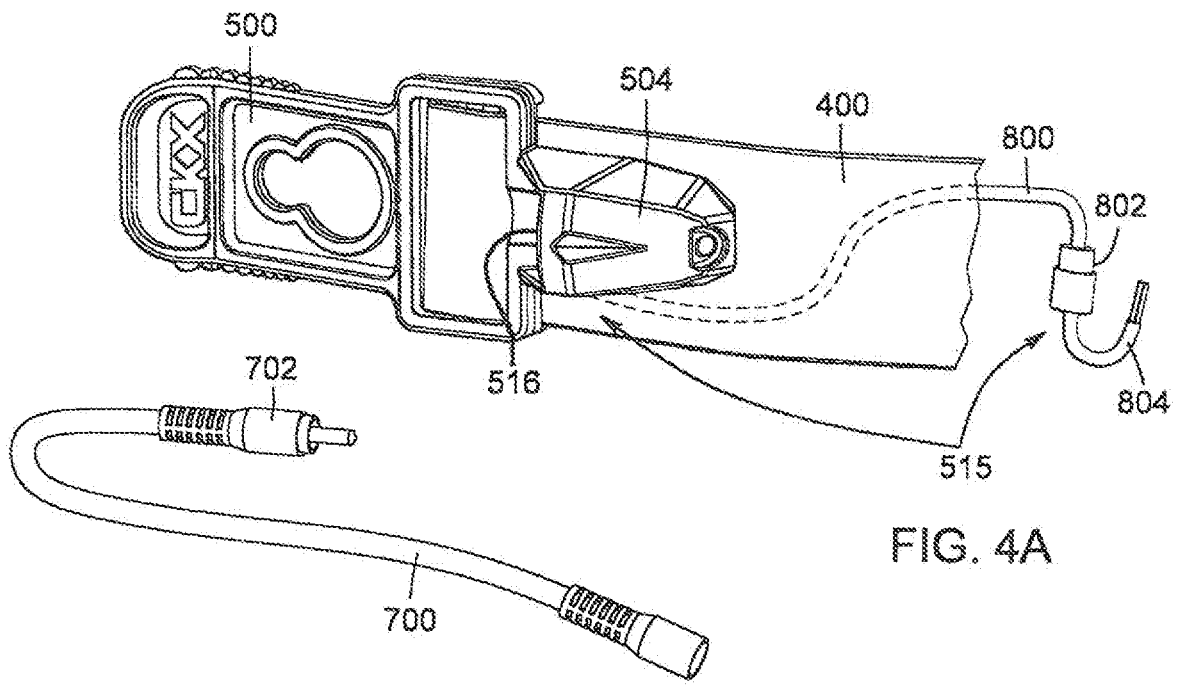
FIG. 4A is a side view of the outer side of a strap of the electric goggle, and of a power cable, in accordance with an embodiment.
Figure 4B:
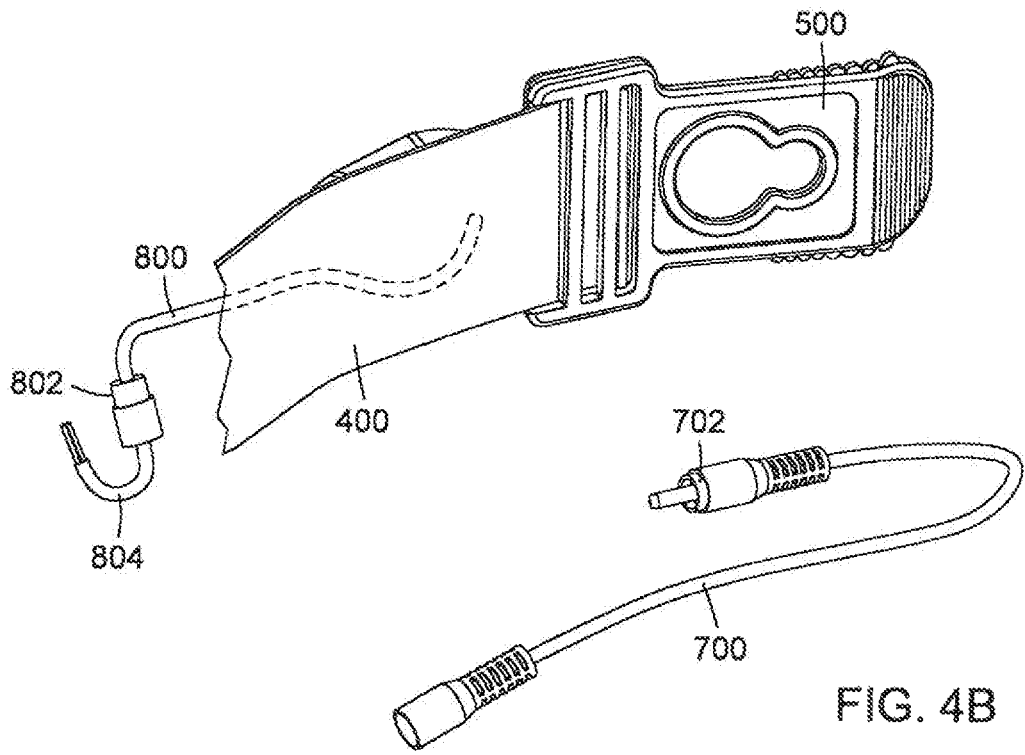
FIG. 4B is a side view of the reverse side of the strap of FIG. 4A, with the power cable.

Now referring to FIGS. 4A and 4B, in addition to FIG. 1, the strap clip 500 is illustratively provided with an electrical assembly 515 adapted to provide power to the conductive elements 302 of the heating assembly of the conductive lens

300. According to one possible embodiment, the electrical assembly 515 comprises an electric socket 516 configured to receive therein a plug 702 of a power cable 700 and at least one electrical wire 800 extending from the electric socket 516 and running along the portion of the resilient strap 406 to connect the electric socket 516 to the conductive elements 302 of the conductive lens 300. The power cable 700 can be plugged to a battery pack positioned on the user, for example in a pocket or a sleeve, for convenience and maneuverability, when the user requires freedom of movement in activities such as skiing for example. Alternatively, the power cable 700 can be plugged directly into a machine the user is using/riding, such as a snowmobile or motorcycle for example, thus providing power to the conductive lens 300.

In an embodiment, the helmet 10 can comprise a battery bracket (not shown) fixedly mounted on said helmet 10. The battery bracket can be adapted for receiving the battery pack therein. In this manner, the conductive elements 302 can be provided with the electrical current needed to heat up the conductive lens 300 and the user can be unencumbered and disconnected from an outer power source such as the aforementioned snowmobile for example. In this embodiment, the battery bracket is preferably positioned so as to not affect the balance of the helmet 10 when being worn by the user, for example, the battery bracket can be positioned substantially in the middle of a back section of the helmet 10. Additionally, the battery bracket position must take into account exposure to the environment, especially in cold weather so as to provide longer lifespan to the battery pack. In this embodiment, the helmet 10 can be provided with a means to recharge the battery pack being retained within the battery bracket of the helmet 10.

Preferably, the electrical assembly 515 can comprise a wire connector 802 and an additional electrical wire 804 connectable to the wire connector 802, extending from the conductive lens 300 towards the resilient strap 400. In this embodiment, the electrical wire 800 and the lens electrical wire 804 are releasably connectable to one another via the wire connector 802 to allow the conductive lens 300 to be interchangeable within the frame 200 without having to completely cut the electrical wire 800 during the process. Alternatively, the electrical wire 800 can be connected directly to the conductive elements 302 of the conductive lens 300 via known methods for connecting wires such as welding for example. In the present embodiment, the electrical wire 800 can be attached to the resilient strap 400 via stitching to fixedly attach the wire 800 to the strap 400. Alternatively, the resilient strap 400 can be folded along a longitudinal direction and sewn together, in order to define a pocket or hem running through the strap 400 through which the electrical wire 800 can extend and thus be secured within the strap 400. In this embodiment, the electrical wire 800 is free to move and extend within the pocket of the strap 400, effectively reducing the risks of damaging or breaking the wire 800 through frequent use of the goggles 100. Other methods for securing the electrical wire 800 to the resilient strap 400 could be used such as staples adapted for electrical wires or any other suitable fasteners.

In a possible embodiment, the conductive lens 300 is not provided with the lens electrical wire 804 in order to connect with the electric socket 516. Instead, the frame 200 can be provided with a plurality of electrical connections, such as connection panels (not shown), arranged around a periphery of the frame 200, onto which the conductive lens 300 can be connected when being mounted on the frame 200. More specifically, the conductive lens 300 can be magnetically mounted on the frame 200, thus connecting the heating elements 302 of the conductive lens 300 to the electrical connections of the frame 200, therefore automatically connecting the heating elements 302 with the electric socket 516 by mounting the lens 300 on the frame 200.

Figure 5A:
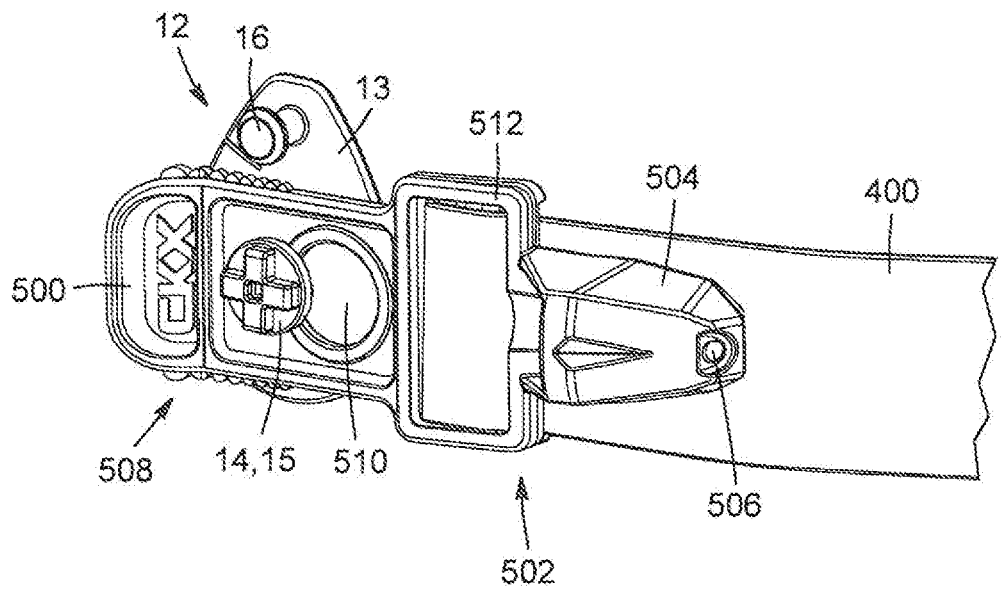
FIG. 5A is a side view of a portion of the strap of the electric goggles, with the strap clip attached to helmet attachment system, in accordance with an embodiment.
Figure 5B:
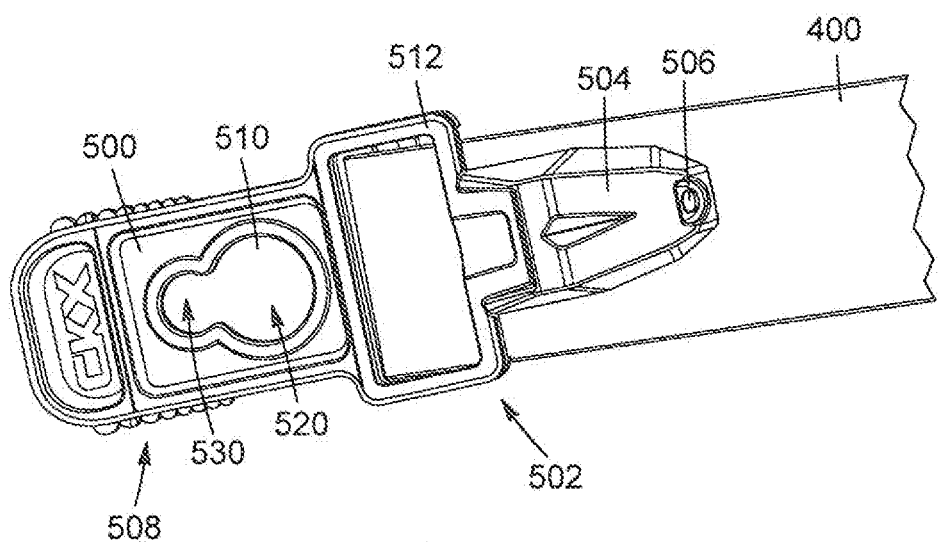
FIG. 5B is another side view of the strap of FIG. 5A, without the attachment assembly.
Figure 6:
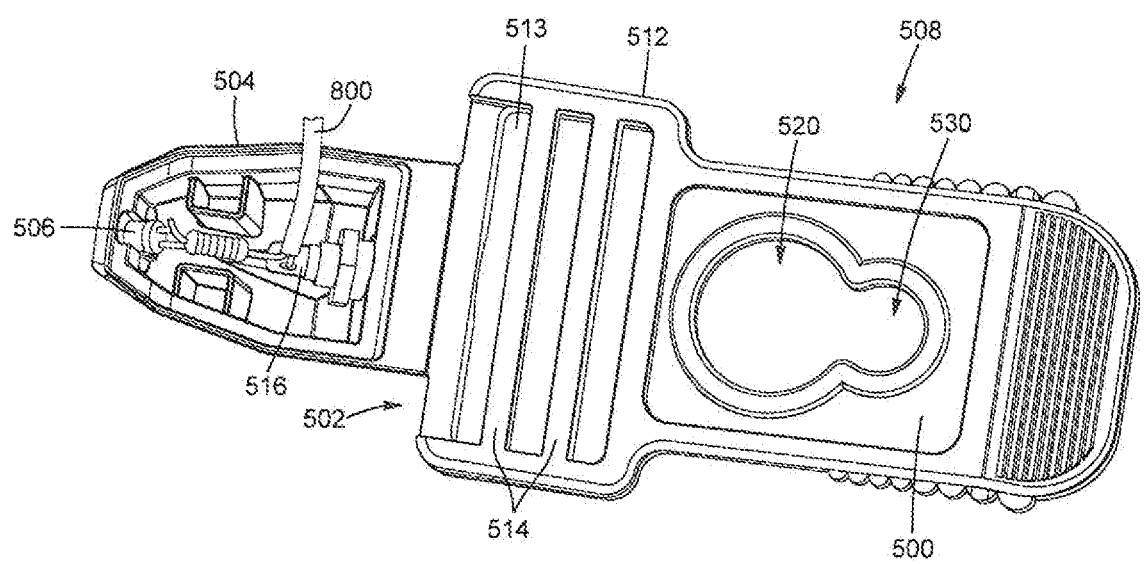
FIG. 6 is an inner view of a socket casing showing electric components, in accordance with an embodiment.
Figure 8A:
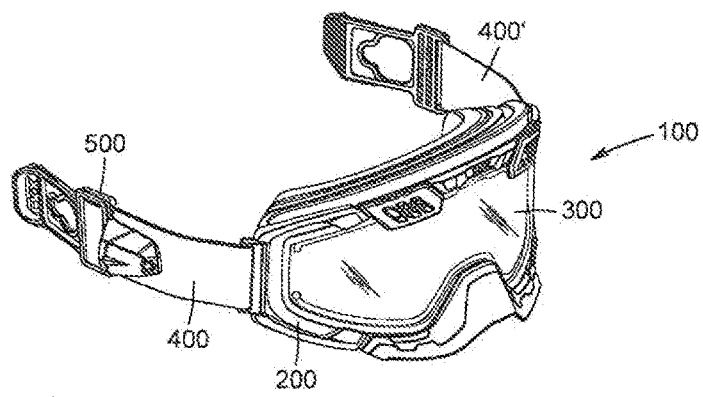
FIG. 8A is a perspective view of a configuration of the electric goggles showing two straps in accordance with an embodiment.
Figure 8B:
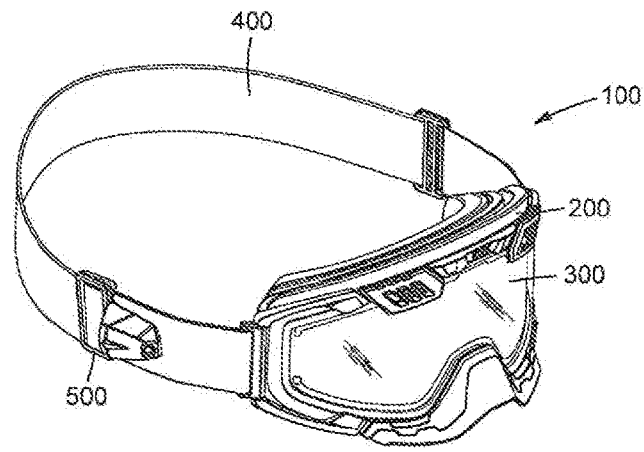
FIG. 8B is a perspective view of a configuration of the electric goggles showing a single strap in accordance with another embodiment.

Now referring to FIGS. 5A to 6, in addition to FIG. 3, the strap clip 500 can comprise a helmet connecting portion 508 configured to removably attach the strap clip 500 to the attachment system 12. In this embodiment, the helmet connecting portion 508 can be provided with a slot 510 which is shaped and sized to allow the helmet stud 14 to pass therethrough and be secured within the slot 510. In this embodiment, the helmet stud 14 comprises two different portions: a first portion adapted to engage a primary opening of the slot 520 and a second portion having a diameter lesser than the diameter of the first portion and adapted to engage a secondary opening of the slot 530. Once the second portion of the helmet stud 14 is engaged within the secondary opening of the slot 530, the first portion of the helmet stud 14 prevents the helmet connecting portion 508 of the strap clip 500 from disconnecting from the attachment system 12 involuntarily.

The strap clip 500 of the present embodiment is further provided with a strap connecting portion 502 for attaching the resilient strap 400 thereto. More specifically, the strap connecting portion 502 can comprise a clip frame 512 defining a clip opening 513 which is provided with at least one cross member 514 extending therethrough, the resilient strap 400 passing through the opening 513 over said at least one cross member 514. This configuration allows the resilient strap 400 to be adjustably attached to the strap clip 500 therefore enabling the user to adjust a length of the resilient strap 400 as needed in a manner as is commonly known in the art. In other possible embodiments, the strap connecting portion 502 can be fixedly attached to the strap 400 by sewing the strap thereto for example.

Now referring back to FIG. 2B, in addition to FIGS. 5A to 6, the electric socket 516 can be contained within a socket casing 504 fixedly positioned on the strap clip 500. More specifically, the socket casing 504 can be integrally molded with the strap connection portion 502 of the strap clip 500 illustratively extending forward from the strap connecting portion 502 in a substantially parallel manner to the resilient strap 400 when the electric goggles 100 are worn. The clip frame, the socket casing and the helmet connecting portion are integrally molded to form a single piece such that a perimeter of the single piece comprises the clip frame, the socket casing and the helmet connecting portion. In a preferred embodiment, the electric socket 516 is so disposed within the socket casing 504 so as to face away from the frame 200 thus having the power cable 700 extend over the pivot point 15 defined by the helmet stud 14 when plugged into the socket 516. This configuration of the power cable 700 unencumbers the user from the power cable 700 when rotating the goggles 100 about the helmet stud 14 in a manner that will be described herein below. In an alternate embodiment, the socket 516 can be positioned to face in any suitable direction, to allow the plug of the power cable 702 to be inserted therein in order to power the electric goggles 100, for example, the electric socket 516 can face downwardly towards the ground. In this embodiment, the electric socket 516 can be an RCA socket. Alternatively, it can be any suitable type of socket, such as a servo-plug socket for example.

In this embodiment, the socket casing 504 can comprise an LED indicator 506 to provide a visual indication if the conductive lens 300 is powered or not. In this embodiment, the LED indicator 506 is positioned opposite the electric socket 516 on the socket casing 504 thus facing the frame 200 to facilitate viewing of the visual LED indicator 506 from an outside perspective. The socket casing 504 may include additional electric components, including electronic chips, such as DIP, QFPs, TSOPs, FGPAs and the likes. The electronic chip can communicate with the LED and/or sensors, such as temperature or humidity sensors provided within the frame or near the lens. The electronic chip may also include a communication module and wireless antenna, to send information regarding the goggle, for example to a smart phone or smart watch.

Now referring to FIGS. 7A and 7B, in addition to FIG. 2B, the electric goggles 100 as described herein above can be used in combination with a strain relief clip 900 designed for reducing the amount of stress and/or strain which can be exerted on the power cable 700 from certain movements. These movements can include moving the goggles 100 on and off the helmet 10 or moving away from the snowmobile while the power cable 700 is connected for example. In the present embodiment, the strain relief clip 900 can be attached to the side of the helmet 10, below the electric socket 516, and comprises an inner channel 902 adapted for the power cable 700 to extend therethrough. The strain relief clip 900 can be made from two complementary components 904 as illustrated in FIGS. 7A and 7B, provided with a fastening mean configured to attach the complementary components 904 to one another in order to hold the power cable 700 therebetween. In this embodiment, one of the complementary components 904 can be provided with a hook 906 while the other can be provided with a hook slot 908, the hook 906 being adapted to extend through the hook slot 908 therefore attaching the complementary components 904 together. Other methods can be used in combination with the hook/hook slot configuration to attach the complementary components 904 together, such as screws, magnets or other suitable fastening means. Once the complementary components 904 are attached to one another about the power cable 700, the strain relief clip 900 can be fixedly attached to the side of the helmet 10 using general fasteners, such as a screw for example. In this embodiment, the complementary components 904 are illustratively provided with an aperture 910 adapted for receiving the aforementioned screw when the components 904 are attached together.

In the present embodiment, the strain relief clip 900 is positioned below the electric socket 516 in order to have the power cable 700, which is extending therethrough, adopt a predetermined orientation when plugged in the electric socket 516. In the illustrated embodiment, a section of the power cable 700 running between the electric socket 516 and the strain relief clip 900 has a "C-shaped" configuration which reduces the strain on the power cable 700 while simultaneously unencumbering the user from said power cable 700 when rotating the goggles 100 about the helmet stud 14. More specifically, the C-shaped section 701 of the power cable 700 is generally adapted to be the only segment of the power cable 700 which moves when the goggles 100 are rotated about the helmet stud 14. In this embodiment, the section of the power cable 700 extending below the strain relief clip 900 and towards the snowmobile or battery pack, is substantially free from movement caused by rotation of the goggles 100, therefore reducing the risk of involuntarily pulling, disconnecting, damaging or otherwise breaking the power cable 700.

In a possible embodiment, the power cable 700 is made from a single cable adapted to extend from the electric socket 516 to a power supply, such as the aforementioned battery pack or snowmobile. In the illustrated embodiments, the power cable 700 is made from multiple segments. For example, the C-shaped section 701, as described hereinabove, can define a first segment which can extend from the electric socket 516 and through the strain relief clip 900, ending just below the strain relief clip 900. A second segment can then be plugged into the first segment of the power cable 700 at one end, and plugged into the power supply at the other, to effectively provide power to the electric goggles 100. In a possible embodiment of the electric goggles 100, the power cable 700 can be configured to be retractable therefore taking up less space when not plugged into the power supply. For example, and without being limitative, the power cable 700 can be adapted to retract within a specific space located on or within the helmet 10, alternatively, the second segment of the power cable 700 can be adapted to retract within, or near the power source, whether it be the battery pack, the snowmobile or any other suitable power source.

In a possible embodiment, the connections provided within the electric goggles 100 can be magnetic to reduce the risk of damaging the wires and/or cables. For example, the connection between the electrical wire 800, wire connector 802 and lens electrical wire 804 can be magnetic. Another example is the connection between the power cable 700 and the electric socket 516, or the power cable 700 and the power supply. Furthermore, as mentioned above, the power cable 700 can be comprised of two segments, in this embodiment, the connection between the two segments can also be magnetic.

Now referring back to FIGS. 1 and 2A, according to one possible embodiment, the electric goggles 100 can be provided with an activation button 760 (FIG. 2A) designed to control the duration and the intensity of the heating of the conductive lens 300. The activation button 750 can be located on the side of the frame 200 for ease of access and convenience, but can alternatively be located elsewhere on the frame 200, on the strap 400, or any suitable location on the electric goggles 100. In this embodiment, the goggles 100 can have two activation modes controlled by the activation button 750: a first mode adapted to provide a constant amount of heat to the conductive lens 300 and a second mode adapted to provide the conductive lens 300 with an intense amount heat for a predetermined amount of time after which the conductive lens 300 will no longer be provided with power from the electrical assembly 515.

Figure 9:
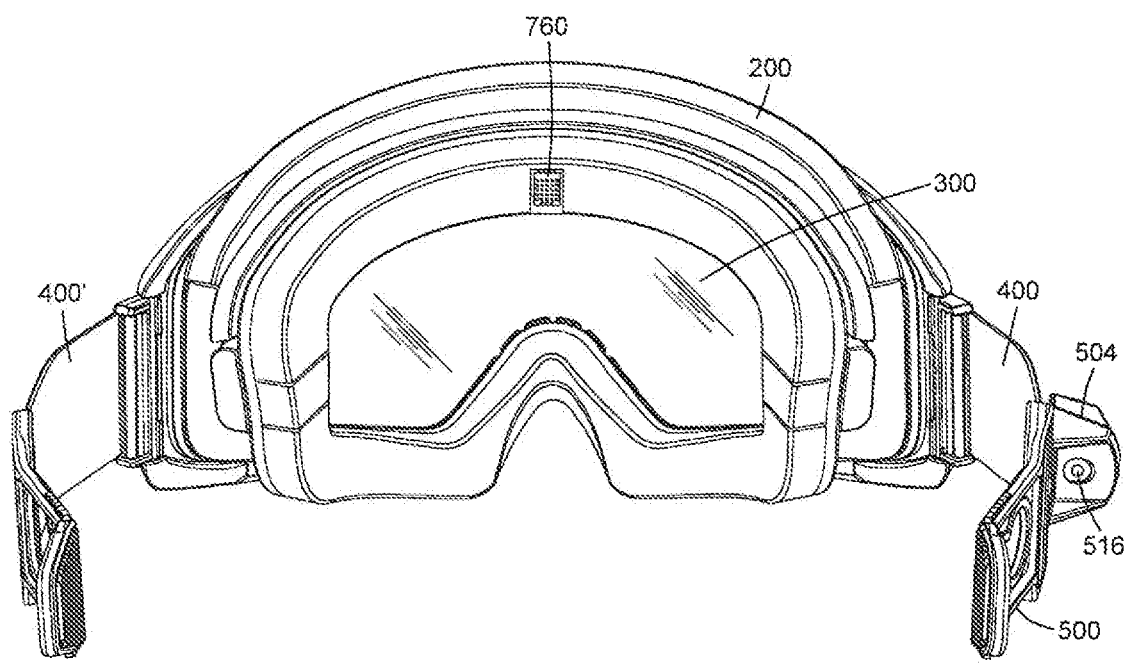
FIG. 9 is an inner view of the electric goggles showing a sensor positioned on the frame in accordance with an embodiment.

Now referring to FIG. 9, in addition to FIG. 2A, in this embodiment, the activation modes can also be controlled via sensors 760 disposed around an inner periphery of the frame 200. The sensors 760 can be adapted to detect humidity levels and/or temperatures within the goggles 100 and programmed to activate the electrical assembly 515 when said humidity levels and/or temperatures reach a predetermined threshold, therefore providing the needed electrical current to the conductive lens 300 to provide heat thereto and prevent or reduce fog accumulation thereon. Of course, the sensors can be located elsewhere on the goggles, and send wired or wireless communications with electronic components within the casing 504 or to other devices, such as a smart phone or smart watch.

It should be understood that the objective of the present disclosure is to present improvements and advantages offered by the electric goggles 100 as described hereinabove. Indeed, the electric socket 616 being located on the strap clip 500 and spaced away from the frame 200 by the portion of the strap 406 presents multiple advantages. Firstly, the power cable 700 extends away from the frame in a predetermined configuration therefore freeing the user from any encumbrance while moving the goggles 100 from the fitted/in use configuration to the rotated configuration. Additionally, the strap clip 500 and electrical assembly 515 barely affect the balance of the helmet, especially while rotating the goggles 100 since they are positioned close to the pivot point 15 as described above. Finally, the use of the strain relief clip 900 in combination with the goggles 100 reduces the risks of damaging or breaking the power cable 700 by biasing the cable in a C-shaped configuration to allow maneuverability of the goggles 100 without tugging or pulling on the power cable 700.

While the electric goggles 100 have been described in conjunction with the exemplary embodiments described above, many equivalent modifications and variations will be apparent to those skilled in the art when given this disclosure.

Accordingly, the exemplary embodiments set forth above are considered to be illustrative and not limiting. The scope of the claims should not be limited by the preferred embodiments set forth in this disclosure, but should be given the broadest interpretation consistent with the description as a whole.

The invention claimed is:

1. Electric goggles for preventing fogging in cold weather conditions, the electric goggles comprising:
   a frame;
   a conductive lens housed within the frame;
   a resilient strap having a frame end and a clip end, the frame end being attached to the frame, the clip end being spaced away from the frame end by a portion of the resilient strap;
   a strap clip comprising:
   a clip frame defining an opening for receiving the clip end and securing the resilient strap to the clip frame;
   a socket casing extending from a first side of the clip frame and having an electric socket for receiving therein a plug of a power cable; and
   a helmet connecting portion extending from a second side of the clip frame and being adapted to removably connect the strap clip to a helmet, wherein the clip frame, the socket casing and the helmet connecting portion are integrally molded to form a single piece such that a perimeter of the single piece comprises the clip frame, the socket casing and the helmet connecting portion; and
   at least one electrical wire running along the portion of the resilient strap extending between the frame and the clip end configured to electrically connect the conductive lens and the electric socket for powering the conductive lens.

2. The electric goggles according to claim 1, comprising a frame fastener connecting the frame end of the resilient strap to the frame.

3. The electric goggles according to claim 1, wherein the electric socket is spaced away from the frame by 1 to 3 inches.

4. The electric goggles according to claim 1, further comprising a wire connector located near the frame end of the resilient strap, allowing for connection and disconnection of the at least one electrical wire from another electrical wire of the conductive lens.

5. The electric goggles according to claim 1, wherein the socket casing is provided with a LED indicator, to visually indicate whether the conductive lens is powered or not.

6. The electric goggles according to claim 1, wherein the electric socket is housed within the socket casing and is adapted to face away from the frame of the electric goggles.

7. The electric goggles according to claim 1, wherein the resilient strap extends from a left side of the frame to a right side of the frame.

8. The electric goggles according to claim 1, wherein the helmet connecting portion comprises a slot defined therethrough, the slot being provided adjacent the opening of the clip frame and spaced from the clip end of the resilient strap passing through the opening of the clip frame.

9. The electric goggles according to claim 1, wherein the resilient strap is a first strap extending from a first side of the frame, and wherein the electric goggles comprise a second strap extending from a second side of the frame, both the first and second straps being connectable to left and right sides of the helmet via respective helmet connecting portions.

10. The electric goggles according to claim 1, wherein the electric socket is an RCA socket.

11. The electric goggles according to claim 1, wherein the electric wire is concealed on a back side of the resilient strap.

12. The electric goggles according to claim 1, wherein the electric wire is sewn in the resilient strap.

13. Electric goggles for use with a helmet having a goggle attachment system, the electric goggles comprising:
   a frame;
   a conductive lens housed in the frame;
   a resilient strap attachable to the frame and extending therefrom; and
   a strap clip comprising:
   a clip frame defining an opening for receiving and securing the resilient strap to the strap clip;
   a helmet connecting portion extending from the clip frame and being removably connectable to the goggle attachment system of the helmet; and
   a socket casing extending from the clip frame and having an electric socket electrically connected to the conductive lens, wherein the clip frame, the socket casing and the helmet connecting portion are integrally molded to form a single piece such that a perimeter of the single piece comprises the clip frame, the socket casing and the helmet connecting portion.

14. The electric goggles according to claim 13, wherein the clip frame comprises at least one bar extending across the opening, the resilient strap passing in and out of the clip frame and looping over the at least one bar for adjusting a length of the resilient strap.

15. The electric goggles according to claim 13, wherein the goggle attachment system of the helmet comprises a stud extending radially from the helmet, and the helmet connecting portion comprises a slot adapted to receive the stud therein for pivotally connecting the strap clip to the helmet.

16. Electric goggles for use with a helmet having an attachment system defining a pivot point on a side of the helmet, the electric goggles comprising:
   a frame;
   a conductive lens housed within the frame, the conductive lens comprising conductive elements and a resistive coating extending between the conductive elements;
   a resilient strap attached to the frame; and
   a strap clip comprising:
   a clip frame configured to secure the resilient strap to the strap clip;
   a helmet connecting portion extending from the clip frame, the helmet connecting portion being removably connectable to the attachment system of the helmet and adapted to pivot about the pivot point; and
   an electric socket electrically connected to the conductive lens, wherein a casing encloses the electric socket, the electric socket being adapted to connect a power cable therein for powering the conductive elements of the conductive lens, wherein the clip frame, the casing and the helmet connecting portion are integrally molded to form a single piece such that a perimeter of the single piece comprises the clip frame, the casing and the helmet connecting portion.

17. The electric goggles according to claim 16, further comprising an electrical wire extending between the electric socket and the conductive elements, and further comprises a wire connector adapted to enable electrically connecting and disconnecting the electrical wire from conductive elements when replacing the conductive lens.

18. The electric goggles according to claim 16, wherein the casing extends along the resilient strap towards the frame.

19. The electric goggles according to claim 18, wherein the casing has an elongated shape which extends generally parallel to the resilient strap.

20. The electric goggles according to claim 16, comprising an activation button configured to control at least one of an intensity and a duration of a current of the conductive elements.

21. The electric goggles according to claim 16, comprising at least one sensor measuring at least one of a temperature and a humidity level within the helmet.

22. The electric goggles according to claim 16, wherein the helmet further comprises a strain relief clip provided below the pivot point, the strain relief clip comprising a channel shaped and adapted to receive the power cable therein.

\* \* \* \* \*